US010619119B2

(12) United States Patent
Hölscher et al.

(10) Patent No.: US 10,619,119 B2
(45) Date of Patent: Apr. 14, 2020

(54) MIXTURES WITH ENRICHED E-ISOMERS OF UNSATURATED MACROCYCLIC MUSK COMPOUNDS

(71) Applicant: SYMRISE AG, Holzminden (DE)

(72) Inventors: Bernd Hölscher, Halle (DE); Wilhelm Wiedmann, Bevern (DE); Sven Siegel, Höxter (DE); Torsten Kulke, Höxter-Lüchtringen (DE)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 15/324,545

(22) PCT Filed: Jul. 7, 2015

(86) PCT No.: PCT/EP2015/065426
§ 371 (c)(1),
(2) Date: Jan. 6, 2017

(87) PCT Pub. No.: WO2016/005360
PCT Pub. Date: Jan. 14, 2016

(65) Prior Publication Data
US 2017/0204350 A1    Jul. 20, 2017

(30) Foreign Application Priority Data
Jul. 7, 2014 (EP) .................................... 14176003

(51) Int. Cl.
| | | |
|---|---|---|
| C11B 9/00 | (2006.01) | |
| A61K 8/35 | (2006.01) | |
| A61Q 19/00 | (2006.01) | |
| A61Q 13/00 | (2006.01) | |

(52) U.S. Cl.
CPC .............. *C11B 9/0038* (2013.01); *A61K 8/35* (2013.01); *A61Q 19/00* (2013.01); *A61K 2800/10* (2013.01); *A61Q 13/00* (2013.01)

(58) Field of Classification Search
CPC ...................................................... C11B 9/0038
See application file for complete search history.

(56) References Cited

U.S. PATENT DOCUMENTS

| | | | |
|---|---|---|---|
| 3,923,699 A | 12/1975 | Komatsu et al. | |
| 2005/0137120 A1* | 6/2005 | Reckziegel | ............. C07C 17/16 512/27 |
| 2008/0319244 A1* | 12/2008 | Surburg | .................. C07C 45/67 585/670 |
| 2013/0303432 A1 | 11/2013 | Hölscher et al. | |

FOREIGN PATENT DOCUMENTS

| | | |
|---|---|---|
| EP | 1 201 738 A1 | 5/2002 |
| EP | 2 662 098 A1 | 11/2013 |

OTHER PUBLICATIONS

Körber et al. ("Influence of Molecular Structure Upon the Musk Odor Characteristics of Macrocyclic Ketones", Fragrance Flavor Subst., Proc. Int. Haarmann Reimer Symp., 2nd (1980), Meeting Date 1979, 155-66). (Year: 1980).*
International Search Report and Written Opinion, PCT/EP2015/065426.

* cited by examiner

*Primary Examiner* — Arrie L Reuther
(74) *Attorney, Agent, or Firm* — Polsinelli PC

(57) ABSTRACT

Herein described are novel mixtures, containing or consisting of a first compound (E) and a second compound (Z), wherein compounds (E) and (Z) are compounds of formula (I) with identical constitutional formula

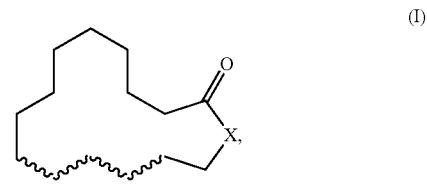

(I)

wherein it applies that one of the four wavy lines denotes a double bond and the remaining wavy lines denote a single bond, respectively, and X is selected from —CH$_2$— and —CH$_2$—CH$_2$—,
and the first compound (E) is trans-configurated and the second compound (Z) is cis-configurated, wherein the weight ratio of compound (E) to compound (Z) in the mixture is in the range of 75:25, preferably of 80:20, to 90:10,
uses of such mixtures, methods for producing such mixtures as well as products containing such mixtures.

14 Claims, No Drawings

MIXTURES WITH ENRICHED E-ISOMERS OF UNSATURATED MACROCYCLIC MUSK COMPOUNDS

CROSS-REFERENCE TO RELATED APPLICATIONS

This application is a national stage application (under 35 U.S.C. § 371) of PCT/EP2015/065426, filed Jul. 7, 2015, which claims benefit of European Application No. 14176003.3, filed Jul. 7, 2014, which are incorporated herein by reference in their entireties.

The present invention primarily relates to novel mixtures, containing or consisting of a first compound (E) and a second compound (Z), wherein compounds (E) and (Z) are compounds of formula (I) with identical constitutional formula

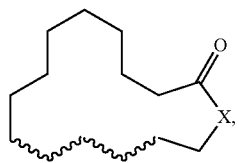

(I)

wherein it applies that one of the four wavy lines denotes a double bond and the remaining wavy lines denote a single bond, respectively, and X is selected from —CH$_2$— and —CH$_2$—CH$_2$—,
and the first compound (E) is trans-configurated and the second compound (Z) is cis-configurated, wherein the weight ratio of compound (E) to compound (Z) in the mixture is in the range of 75:25, preferably of 80:20, to 90:10.

The present invention particularly relates to novel fragrance substance mixtures, preferably in the form of a perfume oil, that preferably furthermore contain one or several additional fragrance substances besides the compounds of formula (I) (as described herein).

Moreover, the present invention relates to perfumed products containing a mixture according to the invention (as described herein), methods for producing mixtures according to the invention, methods for producing perfumed products according to the invention as well as preferred uses of mixtures according to the invention, particularly (a) for masking or reducing the or one or several unpleasant olfactory impressions of one or several unpleasantly smelling substances, and/or (b) for enhancing the or one or several pleasant olfactory impressions of one or several pleasantly smelling substances.

Further aspects and preferred embodiments of the present invention arise from the following description, the examples as well as particularly the enclosed patent claims.

In general, there is an ongoing need on the part of the perfume industry to enhance (emphasise/intensify) pleasant olfactory aspects of fragrance substances and to mask or reduce unpleasant olfactory aspects. Particularly, the fragrance substances described herein that are advantageously preferably to be combined with compounds of formula (I) to be used according to the invention, play an important role in perfumery. Thereby, it is desired to particularly emphasise their natural freshness and/or charisma on one hand and to develop new effects on the other hand.

Thus, it was the primary object of the present invention to provide alternative or preferably improved substances (substances or substance mixtures) for alteration or influencing of olfactory aspects, in particular to specify positive effects in combination with ketones and esters.

These substances thereby preferably ought to meet one, several or preferably all of the following requirements:
easy access,
high efficacy at low concentration, preferably with an inherent odor that is not or hardly detectable at low concentrations,
complete colourlessness or colourlessness to a large extent,
high stability in various mixtures or preparations, wherein in particular no discolouration and/or separation and/or turbidity shall occur,
inert behaviour,
no toxic and/or allergenic effect towards humans.

Furthermore, with the present invention particularly novel, advantageous fragrance substance mixtures, mainly perfume oils, that contain such substances, shall be provided. Such fragrance substance mixtures preferably shall be suitable to fragrance or perfume, respectively, certain products.

Moreover, products perfumed accordingly as well as methods for producing such products shall be provided.

Further objects that underlie the present invention arise from the following explanations and the enclosed patent claims.

The primary object of the present invention is solved by a mixture, containing or consisting of a first compound (E) and a second compound (Z), wherein compounds (E) and (Z) are compounds of formula (I) with identical constitutional formula

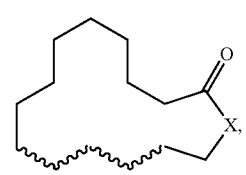

(I)

wherein it applies that one of the four wavy lines denotes a double bond and the remaining wavy lines denote a single bond, respectively, and X is selected from —CH$_2$— and —CH$_2$—CH$_2$—,
and the first compound (E) is trans-configurated and the second compound (Z) is cis-configurated, wherein the weight ratio of compound (E) to compound (Z) in the mixture is in the range of 75:25, preferably of 80:20, to 90:10.

Surprisingly the novel the mixtures (as described herein) are very well suitable to effect a positive influence on (other) fragrance substances, particularly on such fragrance substances as described herein, mainly on ketones and esters.

The compound of formula (I) to be used according to the invention or mixtures as described herein furthermore are advantageously easily accessible or producible. A preferred method (according to the invention) for producing a mixture according to the invention is described further below.

Moreover, the compounds to be used according to the invention or the mixtures according to the invention described herein display a high efficacy already at low concentrations, particularly at concentrations at which the compounds of formula (I) have no or at least only a hardly detectable inherent odor, they advantageously are colourless to a large extent or completely colourless, have high stability in different mixtures or preparations and do not have any toxic and/or allergenic effect on humans.

Furthermore compounds of formula (I) or the mixtures according to the invention described herein, respectively, have the advantage that during their use, particularly a use according to the invention, can be combined with different fragrance substances and perfume oils or usual components of a perfume oil, respectively, to perfume products with any desired scent. Thus, a large selection of scent types can be offered to the consumers by means of the present invention. Fragrance substance mixtures and perfumed products according to the invention containing one or several compounds of formula (I) are described further below.

Preferred according to the invention is a mixture as described above, wherein the mixture comprises one or several compounds selected from the group consisting of cyclohexadecen-1-one, preferably cyclohexadec-8-en-1-one, and cyclopentadec-4-en-1-one, particularly (4Z)-cyclopentadec-4-en-1-one. According to one advantageous embodiment of the present invention, it is preferred if the compounds of formula (I) or at least one compound of formula (I) that are contained in a mixture according to the invention is or are selected from the group consisting of cyclohexadec-8-en-1-one (Aurelione, CAS No. 88642-03-9, 3100-36-5; Globanone, CAS No. 3100-36-5) and (4Z)-cyclopentadec-4-en-1-one (Exaltenon, CAS No. 14595-54-1).

A mixture according to the invention that comprises or consists of a mixture of isomers of trans- and cis-configurated cyclohexadec-8-en-1-one is particularly preferred. Preferably, the weight ratio of compound (E) to compound (Z) (as described herein) in such mixture is in the range of 80:20 to 90:10.

In this context, it shall be exemplarily referred to the following results of the investigation of the olfactory properties of mixtures according to the invention (and comparative mixtures):

The olfactory properties of selected isomer mixtures of cyclohexadec-8-en-1-one can be described as follows:
67% trans-cyclohexadec-8-en-1-one:31% cis-cyclohexadec-8-en-1-one (comparative mixture):
musk-like, erogenous, cosmetic, balsamic odor image and floral aspects
80% trans-cyclohexadec-8-en-1-one: 20% cis-cyclohexadec-8-en-1-one (according to the invention):
musk-like, erogenous, animalistic, reminding of hair
90% trans-cyclohexadec-8-en-1-one: 10% cis-cyclohexadec-8-en-1-one (according to the invention):
musk-like, erogenous, transparent, reminding of hair.
The olfactory properties of selected isomer mixtures of cyclopentadec-4-en-1-one can be described as follows:
3% trans-cyclopentadec-4-en-1-one: 95% cis-cyclopentadec-4-en-1-one (comparative mixture):
musk-like, erogenous, animalistic with a somewhat blunt-powdery nuance reminding of hair
82% trans-cyclopentadec-4-en-1-one: 16% cis-cyclopentadec-4-en-1-one (according to the invention):
musk-like, erogenous, animalistic with a cool, waxy but also dry-wooden note.

Preferably, the mixture according to the invention is a fragrance substance mixture, particularly a perfume oil. Such fragrance substance mixture preferably contains one or several additional fragrance substances. Particularly preferably the additional or one, several or all of the additional fragrance substances is or are selected from the group consisting of alcohols, aldehydes, ketones, ethers, esters and carboxylates, preferably ketones and esters, in particular such with a molar mass the range of 150 to 285 g/mol, preferably of 210 g/mol or less. In the context of the present invention it applies in general that the fragrance substances additionally contained in a fragrance substance mixture according to the invention have a molar mass in the range of 150 to 285 g/mol, preferably of 210 g/mol or less. Fragrance substances to be used particularly preferably are described further below.

In the following, positive influences of the mixtures according to the invention described herein on selected, so-called "measurement fragrance substances" (molecular single fragrance substances as representatives of the chemical functional groups of ketones and esters) are described—exemplarily by means of investigated isomer mixtures of cyclohexadec-8-en-1-one (as described herein):
Ketones:
Methyl ionone, alpha-iso, is the most attractive amongst the isomers of this ketone compound known as "iraldein gamma", with a versatile scent profile that is to be described from soft-wooden over sweet-floral to tobacco-like.

In connection with a 10% proportion (with regard to the total weight of methyl ionone, alpha-iso) of an isomer mixture of cyclohexadec-8-en-1-one (here: 80% trans-cyclohexadec-8-en-1-one: 20% cis-cyclohexadec-8-en-1-one) a scent development is obtained that very authentically reflects the dry-powdery odor of the Parma-violet flower.

Hexahydro naphtalene-ethanone, tetramethyl (isomers), also known under the trivial name "Iso-E-Super", has a warm, ambergris—like wooden smell that reminds of fresh chips of cedarwood.

In combination with 10% (with regard to the total weight of hexahydro naphtalene-ethanone, tetramethyl) of an isomer mixture of cyclohexadec-8-en-1-one (here: 80% trans-cyclohexadec-8-en-1-one:20% cis-cyclohexadec-8-en-1-one) surprisingly creates the powdery, cosmetic scent characters of different iris species in this fragrant substance.
Esters:
Dimethyloctadienyl acetate "linalyl acetate" commonly occurs naturally in ethereal citrus oils and in lavender oils. The scent can be described as fresh, fruity and floral.

A 10% proportion (with regard to the total weight of dimethyloctadienyl acetate "linalyl acetate") of an isomer mixture of cyclohexadec-8-en-1-one (here: 80% trans-cyclohexadec-8-en-1-one:20% cis-cyclohexadec-8-en-1-one) surprisingly enhances a citric, bergamot-like presence of the uniform fragrance substance and strongly increases its efficiency.

Butylcyclohexyl acetate, ortho, tertiary is known under the industrial trivial name "Agrumex". The scent is strong, green and fruity with a slight wooden note reminding of conifers.

The addition of 10% (with regard to the total weight of butylcyclohexyl acetate, ortho, tertiary) of an isomer mixture of cyclohexadec-8-en-1-one (here: 90% trans-cyclohexadec-8-en-1-one:10% cis-cyclohexadec-8-en-1-one) strongly enhances the scent profile towards a fruity note that reminds of green apple peels and strongly eliminates the slightly rough, camphor-like wooden note described initially.

Within the scope of the present invention, the "measurement fragrance substances" described above are particularly preferably used fragrance substances in combination with compounds of formula (I) (as described herein) in fragrance substance mixtures according to the invention.

In connection with the fragrance substance mixtures according to the invention described herein it applies that the ratio of the total mass of fragrance substances that do not correspond to formula (I) to the total mass of compound(s) of formula (I) preferably is higher or equal to 80:20, preferably higher or equal to 90:10, particularly preferably higher than or equal to 95:5. Particularly preferred amount (-ratios) according to the invention arise from the enclosed examples.

Fragrance substance mixtures according to the invention are usually liquid at 25° C. and 1013 hPa and normally are homogeneous solutions.

Fragrance substance mixtures, particularly perfume oils, often comprise synthetic or natural (preferably) taste and odor neutral carrier oils, which contain the scent or fragrance substance (as artificial or natural substances) in highly concentrated form (as well as perfumistic solvents and/or auxiliary materials, if applicable). The same applies accordingly to the fragrance substance mixtures according to the invention described herein.

Perfume oils (as preferred embodiment of fragrance substance mixtures (according to the invention)) often serve scent applications. Perfumes, for example, are produced with perfume oils by adding them to (e.g. alcoholic) solutions that "carry away" the scent- or fragrance substance during evaporation and thus convey the sensory impression of a certain odor to the olfactory organ of the user, i.e. the person. Such mixtures can be, for example, a perfume, eau de parfum or eau de toilette. Furthermore, perfume oils serve the generation of a certain scent in living rooms, such as for example during the use of fragrance lamps, nebulizers or diffusers. Furthermore, perfume oils can also be used in a variety of further products or preparations, respectively, for example in shoe creams to hair shampoos, sanitary towels to toilet cleaners, face creams to washing powder and cat stones.

Examples for fragrance substances that generally preferably can be used as component of a fragrance substance mixture according to the invention, particularly a perfume oil according to the invention, can be found for example in S. Arctander, Perfume and Flavor Chemicals, Vol. I and II, Montclair, N.J., 1969, author's edition or H. Surburg, J. Panten, Common Fragrance and Flavor Materials, $5^{th}$ Ed., Wiley-VCH, Weinheim 2006.

Preferred ethereal oils, concretes, absolutes, resins, resinoids, balsams and/or tinctures, that can be a component of a fragrance substance mixture according to the invention, particularly a perfume oil according to the invention, are preferably to be selected from the group consisting of:

Ambergris tincture; amyris oil; angelica seed oil; angelica root oil; aniseed oil; valerian oil; basil oil; tree moss absolute; bay oil; mugwort oil; benzoin resin; bergamot oil; beeswax absolute; birch tee oil; bitter almond oil; savory oil; bucco leaf oil; cabreuva oil; cade oil; calmus oil; camphor oil; cananga oil; cardamom oil; cascarilla oil; cassia oil; cassie absolute; castoreum absolute; cedar leaf oil; cedar wood oil; cistus oil; citronella oil; citrus oil; copaiva balsam; copaiva balsam oil; coriander oil; costus root oil; cumin oil; cypress oil; davana oil; dill weed oil; dill seed oil; eau de brouts absolute; oakmoss absolute; elemi oil; estragon oil; eucalyptus citriodora oil; eucalyptus oil; fennel oil; spruce needle oil; galbanum oil; galbanum resin; geranium oil; grapefruit oil; guaiacwood oil; gurjun balsam; gurjun balsam oil; helichrysum absolute; helichrysum oil; ginger oil; iris root absolute; iris root oil; jasmine absolute; calamus oil; chamomile oil blue; chamomile oil roman; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; lime oil distilled; lime oil squeezed; linaloe oil; litsea cubeba oil; bay leaf oil; macis oil; Marjoram oil; mandarin oil; massoia bark oil; mimosa absolute; musk seed oil; musk tincture; muscatel sage oil; nutmeg oil; myrrh absolute; myrrh oil; myrtle oil; carnation leaf oil; carnation blossom oil; neroli oil; olibanum absolute; olibanum oil; opopanax oil; orange blossom absolute; orange oil; origanum oil; palmarosa oil; patchouli oil; perilla oil; peru balsam oil; parsley leaf oil; parsley seed oil; petitgrain oil; peppermint oil; pepper oil; allspice oil; pine oil; poley oil; rose absolute; rosewood oil; rose oil; rosemary oil; sage oil Dalmatian; sage oil Spanish; sandalwood oil; celery seed oil; spike lavender oil; star aniseed oil; styrax oil; tagetes oil; fir needle oil; tea tree oil; turpentine oil; thyme oil; tolu balsam; tonka absolute; tuberose absolute; vanilla extract; violet leaf absolute; verbena oil; vetiver oil; juniper berry oil; wine yeast oil; vermouth oil; wintergreen oil; ylang oil; ysop oil; civet absolute; cinnamon leaf oil; cinnamon bark oil.

Preferred single fragrance substances that can be preferably used as component of a fragrance substance mixture according to the invention, particularly of a perfume oil according to the invention, are selected from the group of hydrocarbons, thereby preferred 3-carene; α-pinene; β-pinene; α-terpinenes; γ-terpinenes; p-cymene; bisabolene; camphene; caryophyllene; cedrene; farnesene; limonene; longifolene; myrcene; ocimene; valencene; (E,Z)-1,3,5-undecatriene; styrene; diphenylmethane;

aliphatic alcohols, thereby preferred hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

aliphatic aldehydes and their acetals, thereby preferred hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethylacetal; 1,1-dimethoxy-2,2,5-trimethyl-4-hexene; citronellyl oxyacetaldehyde; 1-(1-methoxy-propoxy)-(E/Z)-3-hexene;

aliphatic ketones and their oximes, thereby preferred 2-heptanone; 2-octanone; 3-octanone; 2-nonanone; 5-methyl-3-heptanone; 5-methyl-3-heptanone oxime; 2,4,4,7-tetramethyl-6-octene-3-one; 6-methyl-5-heptene-2-one;

aliphatic sulphur-containing compounds, thereby preferred 3-methylthio-hexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

aliphatic nitriles, thereby preferred 2-nonenoic acid nitrile; 2-undecenoic acid nitrile; 2-tridecenoic acid nitril; 3,12-tridecadienoic acid nitrile; 3,7-dimethyl-2,6-octadienoic acid nitrile; 3,7-dimethyl-6-octenoic acid nitril;

esters of aliphatic carboxylic acids, thereby preferred (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl-isobutyrate; hexyl crotonate; ethyl isovalerate; ethyl-2-methylpentanoate; ethyl hexanoate; allyl hexanoate; ethyl heptanoate; allyl heptanoate; ethyl octanoate; ethyl-(E,Z)-2,4- decadienoate; methyl-2-octinate; methyl-2-noninate; allyl-2-isoamyl oxyacetate; methyl-3,7-dimethyl-2,6-octadienoate; 4-methyl-2-pentyl-crotonate;

acyclic terpene alcohols, thereby preferred citronellol; geraniol; Nerol; linalool; lavadulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; as well as their formates, acetates, propionates, isobutyrates, butyrates, isovalerianates, pentanoates, hexanoates, crotonates, tiglinates and 3-methyl-2-butenoates;

acyclic terpene aldehydes and -ketones, thereby preferred geranial; neral; citronellal; 7-hydroxy-3,7-dimethyloctanal; 7-methoxy-3,7-dimethyloctanal; 2,6,10-trimethyl-9-undecenal; geranyl acetone; as well as the dimethyl- and diethyl acetals of geranial, neral, 7-hydroxy-3,7-dimethyloctanal;

cyclic terpene alcohols, thereby preferred isopulegol; alpha-terpineol; terpinenol-4; menthan-8-ol; menthan-1-ol; menthan-7-ol; borneol; isoborneol; linalool oxide; nopol; cedrol; ambrinol; vetiverol; guaiol; as well as their formates, acetates, propionates, isobutyrates, butyrates, isovalerianates, pentanoates, hexanoates, crotonates, tiglinates and 3-methyl-2-butenoates; menthyl formate; menthyl propionate; menthyl butyrate; menthyl isobutyrate; menthyl isovalerianate; menthyl hexanoate; menthyl crotonate; menthyl tiglinate;

cyclic terpene aldehydes and -ketones, thereby preferred menthone; isomenthone; 8-mercaptomenthan-3-one; carvone; camphor; fenchone; alpha-ionone; beta-ionone; beta-n-methyl ionone; beta-isomethyl ionone; alpha-irone; alpha-damascone; beta-damascone; beta-damascenone; delta-damascon; gamma-damascon; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedarwood oil (methyl cedryl ketone);

cyclic alcohols, thereby preferred 4-tert.-butylcyclohexanol; 3,3,5-trimethylcyclohexanol; 3-isocamphylcyclohexanol; 2,6,9-trimethyl-Z2,Z5,E9-cyclodedecatrien-1-01; 2-isobutyl-4-methyltetrahydro-2H-pyran-4-ol;

cycloaliphatic alcohols, thereby preferred alpha,3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-01; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

cyclic and cycloaliphatic ethers, thereby preferred cineol; cedryl methyl ether; cyclododecyl methyl ether; 1,1-dimethoxycyclododecane; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

cyclic and macrocyclic ketones, thereby preferred 4-tert.-butyl cyclohexanone; 2,2,5-trimethyl-5-pentyl cyclopentanone; 2-heptyl cyclopentanone; 2-pentyl cyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4(5H)-indanone; 8-cyclohexadecen-1-one; 9-cycloheptadecen-1-one; cyclopentadecanone; cyclohexadecanone;

cycloaliphatic aldehydes, thereby preferred 2,4-dimethyl-3-cyclohexene carbaldehyde; 2-methyl-4-(2,2,6-trimethyl-cyclohexen-1-yl)-2-butenal; 4-(4-hydroxy-4-methylpentyl)-3-cyclohexene carbaldehyde; 4-(4-methyl-3-penten-1-yl)-3-cyclohexene carbaldehyde;

cycloaliphatic ketones, thereby preferred 1-(3,3-dimethyl-cyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphtalenylmethylketone; methyl-2,6,10-trimethyl-2,5,9-cyclododecatrienylketone; tert.-butyl-(2,4-dimethyl-3-cyclohexen-1-yl)ketone;

esters of cyclic alcohols, thereby preferred 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5, or 6-indenyl acetate; 4,7-methano-3a,4,5,6,7,7a-hexahydro-5, or 6-indenyl propionate; 4,7-methano-3a,4,5,6,7,7a-hexahydro-5, or 6-indenyl isobutyrate; 4,7-methanooctahydro-5, or 6-indenyl acetate;

esters of cycloaliphatic alcohols, preferably 1-cyclohexylethyl crotonate;

esters of cycloaliphatic carboxylic acids, thereby preferred allyl-3-cyclohexyl propionate; allyl cyclohexyloxy acetate; cis- and trans-methyldihydrojasmonate; cis- and trans-methyljasmonate; methyl-2-hexyl-3-oxocyclopentane carboxylate; ethyl-2-ethyl-6,6-dimethyl-2-cyclohexene carboxylate; ethyl-2,3,6,6-tetramethyl-2-cyclohexene carboxylate; ethyl-2-methyl-1,3-dioxolane-2-acetate;

aralipathic alcohols, thereby preferred benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentan-1-ol; 3-methyl-5-phenylpentanol; 3-phenyl-2-propen-1-ol; 4-methoxybenzyl alcohol; 1-(4-isopropylphenyl)ethanol;

esters of araliphatic alcohols and aliphatic carboxylic acids, thereby preferred benzyl acetate; benzyl propionate; benzyl isobutyrate; benzyl isovalerianate; 2-phenylethyl acetate; 2-phenylethyl propionate; 2-phenylethyl isobutyrate; 2-phenylethyl isovalerianate; 1-phenylethyl acetate; alpha-trichloromethyl benzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

araliphatic ethers, thereby preferred 2-phenylethyl methyl ether; 2-phenylethyl isoamyl ether; 2-phenylethyl-1-ethoxyethyl ether; phenyl acetaldehyde dimethyl acetal; phenyl acetaldehyde diethyl acetal; hydratropic aldehyde dimethyl acetal; phenyl acetaldehyde glyceryl acetal; 2,4,6-trimethyl-4-phenyl-1,3-dioxane; 4,4a,5,9b-tetrahydroindeno[1,2-d]-m-dioxine; 4,4a,5,9b-tetrahydro-2,4-dimethylindeno[1,2-d]m-dioxine;

aromatic and araliphatic aldehydes, thereby preferred benzaldehyde; phenyl acetaldehyde; 3-Phenyl propanal; hydratropic aldehyde; 4-methyl benzaldehyde; 4-methylphenyl acetaldehyde; 3-(4-ethylphenyl)-2,2-dimethyl propanal; 2-methyl-3-(4-isopropylphenyl)propanal; 2-methyl-3-(4-tert.-butylphenyl)propanal; 2-methyl-3-(4-isobutylphenyl) propanal; 3-(4-tert.-butylphenyl)propanal; cinnamic aldehyde; alpha-butyl cinnamic aldehyde; alpha-amyl cinnamic aldehyde; alpha-hexyl cinnamic aldehyde; 3-methyl-5-phenylpentanal; 4-methoxy benzaldehyde; 4-hydroxy-3-ethoxy benzaldehyde; 3,4-methylendioxy benzaldehyde; 3,4-dimethoxy benzaldehyde; 2-methyl-3-(4-methoxyphenyl)propanal; 2-methyl-3-(4-methylendioxyphenyl)propanal;

aromatic and araliphatic ketones, thereby preferred acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanone; 2-benzofuranylethanone; (3-methyl-2-benzofuranyl)ethanone; benzophenone; 1,1,2,3,3,6-hexamethyl-5-indanylmethylketone; 6-tert.-butyl-1,1-dimethyl-4-indanylmethylketone; 1-[2,3-dihydro-1,1,2,6-tetramethyl-3-(1-methylethyl)-1H-5-indenyl]ethanone; 5',6',7,8'-tetrahydro-3',5',5',6',8',8'-hexamethyl-2-acetonaphthone;

aromatic and araliphatic carboxylic acids and their esters, thereby preferred benzoic acid; Phenylacetic acid; methyl benzoate; ethyl benzoate; hexyl benzoate; methyl phenylacetate; ethyl phenylacetate; geranyl phenylacetate; phenylethyl-phenyl acetate; methyl cinnamate; ethyl cinnamate; benzyl cinnamate; phenylethyl cinnamate; cinnamyl cinnamate; allylphenoxy acetate; methyl salicylate; isoamyl salicylate; hexyl salicylate; cyclohexyl salicylate; cis-3-hexenyl salicylate; benzyl salicylate; phenylethyl salicylate; methyl-2,4-dihydroxy-3,6-dimethyl benzoate; ethyl-3-phenylglycidate; ethyl-3-methyl-3-phenylglycidate;

nitrogen-containing aromatic compounds, thereby preferred 2,4,6-trinitro-1,3-dimethyl-5-tert.-butylbenzene; 3,5-dinitro-2,6-dimethyl-4-tert.-butyl acetophenone; cinnamic acid nitrile; 3-methyl-5-phenyl-2-pentenoic acid nitrile; 3-methyl-5-phenylpentanoic acid nitrile; methyl anthranilate; methy-N-methyl anthranilate; Schiff bases of methyl anthranilate with 7-hydroxy-3,7-dimethyloctanal, 2-methyl-3-(4-tert.-butylphenyl)propanal or 2,4-dimethyl-3-cyclohexene carbaldehyde; 6-isopropyl chinolin; 6-isobutyl chinolin; 6-sec.-butyl chinolin; 2-(3-phenylpropyl)pyridine; indole; skatole; 2-methoxy-3-isopropyl pyrazine; 2-isobutyl-3-methoxy pyrazine;

phenols, phenyl ethers and phenyl esters, thereby preferred estragol; anethol; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenyl acetate;

heterocyclic compounds, thereby preferred 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

lactones, thereby preferred 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene-1,13-tridecandioate; coumarin; 2,3-dihydrocoumarin; octahydrocoumarin.

Particularly preferred is a fragrance substance mixture according to the invention, wherein the amount of mixture according to the invention or the amount of compound (E) and compound (Z) (as described herein) is sufficient (a) to mask or reduce the or one or several unpleasant olfactory impression(s) of another fragrance substance in the fragrance substance mixture,
and/or (b) to enhance the or one or several pleasant olfactory impression(s) of another fragrance substance in the fragrance substance mixture.

It is also particularly preferred if the total amount of compounds of formula (I) with regard to the total weight of the fragrance substance mixture is 1 wt. % or less, preferably 0.1 wt. % or less, particularly preferably 0.001 wt. % or less.

Another aspect of the present invention relates to a perfumed product, containing a mixture according to the invention as described herein, preferably a fragrance substance mixture according to the invention, particularly a perfume oil, in a sensorially effective amount, wherein the proportion of the mixture or of the fragrance substance mixture or of the compounds of formula (I) with regard to the total weight of the product preferably is in the range of 0.01, preferably 0.1, to 20, preferably 10 wt. %, preferably in the range of 0.1 to 5 wt. %, particularly preferably in the range of 0.25 to 3 wt. %.

What has been stated above applies accordingly to compounds of formula (I) that preferably are to be used or contained as well as, if applicable, to further components of a contained fragrance substance mixture.

For purposes of clarification it has to be mentioned that (perfumed) products according to the invention within the scope of the present text are to be understood as products that have been caused or produced on purpose, but not as naturally occurring substance mixtures, for example such as the ones that can be obtained from plant-based starting materials by means of extraction.

Preferred products are for example perfume extraits, eau de parfums, eau de toilettes, aftershaves, eau de colognes, pre-shave products, splash colognes and perfumed refreshing tissues as well as perfumed or to be perfumed acidic, alkaline and neutral detergents, such as e.g. floor cleaners, window glass cleaners, dishwashing detergents, bathroom and sanitary cleaners, scouring agent, solid or liquid toilet cleaners, toilet sticks, toilet stones (liquid or solid), powdery or foamy carpet cleaners, liquid detergents, powdery detergents, laundry pretreatment agents such as bleaches, soaking agents and stain removers, fabric softeners, laundry soaps, laundry tablets, disinfectants, surface disinfectants as well as air improvers in liquid or gel-like form or applied to a solid carrier, particularly for deodorization of exhaust air from air conditioning and industrial processes, as well as air improvers in the form of aerosol or pump sprays, waxes and polishes such as furniture polishes, floor waxes, shoe creams, strengthening, impregnating or deodorizing textile treatment agents, diapers, sanitary towels, panty liners, plasters, as well as personal care agents such as e.g. solid and liquid soaps, shower gels, shampoos, shaving soap, shaving foams, bathing oils, damp cleaning cloths, cosmetic emulsion of the oil-in-water, water-in-oil and water-in-oil-in-water type such as e.g. skin creams and lotions, face creams and lotions, sun protection creams and lotions, after sun creams and lotions, hand creams and lotions, foot creams and lotions, depilatory creams and lotions, aftershave creams and lotions, tanning creams and lotions, hair care products such as e.g. hair sprays, hair gels, strengthening hair lotions, hair conditioners, permanent or semi-permanent hair dyes, hair forming agents such as cold waves and hair smoothing agents, hair tonics, hair creams and lotions, deodorants and antiperspirants such as e.g. armpit sprays, roll-ons, deo sticks, deo creams, products for decorative cosmetic such as e.g. eyeshadow, makeups, lipsticks, mascara as well as candles, lamp oils, incense sticks, animal litter, cat litter, insecticides, repellents, liquid and gaseous fuels, heating oils and heating gases.

Particularly preferred is a product according to the invention selected from the group consisting of perfume extraits, eau de parfums, eau de toilettes, aftershaves, eau de colognes, pre-shave products, splash colognes, perfumed refreshing tissues, acidic, alkaline and neutral detergents, textile fresheners, ironing aids, liquid detergents, powdery detergents, laundry pretreatment agents, fabric softeners, laundry soaps, laundry tablets, disinfectants, surface disinfectants, air improvers, aerosol sprays, waxes and polishes, personal care agents, hand creams and lotions, foot creams and lotions, depilatory creams and lotions, aftershave creams and lotions, tanning creams and lotions, hair care products, deodorants and antiperspirants, products for decorative cosmetic, candles, lamp oils, incense sticks, insecticides, repellents and fuels.

A product that shall be olfactorily improved by means of reduction of an unpleasant smell (particularly as described above) or by enhancement of a pleasant olfactory aspect (particularly as described herein) can underlie a product according to the invention.

According to a preferred embodiment, the compounds of formula (I) to be used according to the invention or corresponding mixtures thereof or fragrance substance mixtures (as described herein) are adsorbed to a carrier substance that guarantees a fine distribution of compounds inside the product as well as a controlled release during application. Such carriers may be porous inorganic materials such as silica gels, zeolites, gypsums, clay, clay granules, aerated concrete etc. or organic materials such as woods and cellulose-based substances.

The compounds of formula (I) to be used according to the invention or corresponding mixtures thereof or fragrance substance mixtures (as described herein) may also be present in microencapsulated or spray-dried form, as inclusion complexes or as extrusion products and can be added to a product in this form.

If applicable, the properties of such modified compounds of formula (I) to be used according to the invention or of corresponding mixtures thereof or of fragrance substance mixtures (as described herein) can be further optimized by means of so-called "coating" with suitable materials with regard to a more targeted release, wherein preferably wax-like plastic materials such as e.g. polyvinyl alcohol are used.

A microencapsulation of the compounds of formula (I) to be used according to the invention or of corresponding mixtures thereof or of fragrance substance mixtures (as described herein) can take place, for example, by means of the so-called coacervation process with the aid of capsule materials, e.g. of polyurethane-like substances or soft gelatin. Spray-dried compounds of formula (I) can be produced, for example, by means of spray-drying of a substance to be used according to the invention, i.e. of an emulsion or dispersion containing an alcohol of the compound of formula (I) or a corresponding mixture, wherein modified starches, proteins, dextrins and/or plant-based gums can be used as carrier substance. Inclusion complexes can be produced, for example, by means of addition of dispersions, which are or comprise compounds of formula (I) to be used according to the invention or corresponding mixtures thereof, and cyclodextrins or urea derivatives into a suitable solvent, e.g. water. Extrusion products can take place by means of fusion of compounds of formula (I) to be used according to the invention or corresponding mixtures with a suitable wax-like substance and extrusion with subsequent solidification, in a suitable solvent, e.g. isopropanol, if applicable.

The compounds of formula (I) to be used according to the invention or corresponding mixtures thereof or fragrance substance mixtures (as described herein) can be used in many preparations or products, wherein they are preferably combined with one or several of the following excipients or active ingredients:

Preserving agents, abrasives, anti-acne agents, agents against skin aging, antibacterial agents, anticellulite agents, antidandruff agents, anti-inflammatory agents, irritation preventing agents, irritation inhibiting agents, antimicrobial agents, antioxidants, astringents, sweat inhibiting agents, antiseptic agents, antistatic agents, binders, buffers, carrier materials, chelate builders, cell stimulants, cleaning agents, caring agents, depilatory agents, surface active agents, deodorizing agents, antiperspirants, plasticizers, emulsifiers, enzymes, ethereal oils, fibres, fixators, foam builders, foam stabilizers, substances to prevent foaming, foam boosters, fungicides, gelatinizing agents, gelforming agents, hair care products, hair forming products, smoothing agents, moisturizing agents, dampening substances, moist-keeping substances, bleaching agents, (textile-)strengthening agents, stain removing agents, optical brightening agents, impregnating agents, dirt-repellent agents, friction-lowering agents, lubricants, moisturizing creams, ointments, opacifiers, plasticizing agents, covering agents, polish, glazing agents, polymers, powders, proteins, regreasing substances, abrasive agents, silicones, skin soothing agents, skin cleaning agents, skin caring agents, skin healing agents, skin lightening agents, skin protecting agents, skin softening agents, cooling agents, skin cooling agents, warming agents, skin warming agents, stabilizers, UV-absorbing agents, UV-filters, detergents, fabric softeners, suspending agents, skin tanning agents, thickening agents, vitamins, oils, waxes, fats, phospholipids, saturated fatty acids, mono- or polyunsaturated fatty acids, a-hydroxy acids, polyhydroxy fatty acids, liquefying agents, dyes, color-protecting agents, pigments, anticorrosives, aromas, flavorings, aromatic substances, polyols, surfactants, electrolytes, organic solvents or silicon derivatives.

According to one embodiment of the present invention a preferred product according to the invention, particularly a deodorant or the like, additionally contains (depending on the desired mode of action) one or several of the following active substances:

(1) antimicrobially active substances that inhibit the development of microorganisms that are responsible for the smell of perspiration; for example Triclosan® (5-chloro-2-(2,4-dichlorophenoxy)phenol), triclocarban, chlorhexidine, chlorhexidine hydrochloride, chlorhexidine diacetate, chlorhexidine digluconate, 2-phenoxyethanol, farnesol, glycerin esters and -ethers such as glyceryl monolaurate, glyceryl monocaprinate, hexoxyglycerin, octoxyglycerin (=ethylhexylglycerin, 3-(2-ethylhexyloxy-1,2-propanediol) or Sensiva® SC 50 (by Schülke & Mayr), aliphatic 1,2-diols such as e.g. 1,2-decanediol (EP 1 269 983), aralipathic alcohols such as for example described in EP 799 174, preferably 4-methyl-4-phenyl-2-pentanol (Vetikol; WO 03/024907) or 2-methyl-4-phenyl-2-butanol (1,1-dimethyl-3-phenylpropanol, alpha,alpha-dimethylphenethylcarbinol), l-menthyl methyl ether as described in WO 02/41861, 2-benzylheptan-1-ol (Jasmol; 2-n-pentyl-3-phenylpropan-1-ol), 2,2-dimethyl-3-phenylpropanol (muguet alcohol; cf. U.S. Pat. No. 4,091, 090), antimicrobially active secondary alcohols, such as for example described in WO 2005/004601, particularly 3-methyl-6-phenyl-2-hexanol, 4-(2,4-dimethylphenyl)-2-butanol, 6-(4-isopropylphenyl)-3-methyl-2-hexanol, 4-(2, 4,5-trimethylphenyl)-2-butanol, 3,3-dimethyl-4-phenyl-2-butanol, 3-methyl-4-(2-methylphenyl)-2-butanol, 6-(3, 4-dimethylphenyl)-2-hexanol, aliphatic carboxylic acids such as 2-hexyloctanoic acid, 2-hexyldecanoic acid, 2-butyloctanoic acid or 2-butyldecanoic acid;
(2) enzyme inhibiting substances that inhibit the effect of enzymes that participate in the formation of smell of perspiration; for example citric acid esters and metal-chelating substances such as EDTA (ethylenediaminetetraacetic acid), EGTA [ethylenebis(oxyethylenenitrilo)-tetraacetic acid] and DTPA (diethylenetriaminepentaacetic acid, pentetic acid);
(3) odor absorbing substances that absorb substances that are responsible for the smell of perspiration; for example zinc rizinoleate, cyclodextrins;
(4) antiperspirants that inhibit sweat secretion and thus eliminate the breeding grounds of bacteria that are responsible for body odor. Astringent metal salts are generally preferably used as antiperspirants, particularly inorganic and organic metal salts of the elements aluminium, zinc, magnesium, tin and zircon as well as their mixtures, wherein particularly halogenides such as aluminium chloride, alkaline aluminium hydroxychlorides, zirconyl oxychlorides and zirconyl hydroxychlorides as well as their mixtures are used. Often these aluminium and zirconium salts and mixtures thereof are also used in a complexed form, wherein as complex builders preferably propylene glycol, polyethylene glycol or glycine are used.

The present invention also relates to a method for producing a perfumed product, particularly a perfumed product according to the invention as described herein, comprising the following steps:
i) Providing a mixture or a fragrance substance mixture according to the invention or a first compound (E) and a second compound (Z) as defined herein, in a weight ratio as defined herein according to the invention,
ii) providing one or several further components of the perfumed product to be produced (particularly such as described above), and
iii) contacting or mixing the further components provided in step ii) with a sensorially effective amount of the components provided in step i).

As follows from the explanations further above, the mixtures according to the invention, particularly such as described herein as preferred, are suited as odor modifiers, preferably
(a) for masking or reducing the or one or several unpleasant olfactory impressions of one or several unpleasantly smelling substances, and/or
(b) for enhancing the or one or several pleasant olfactory impressions of one or several pleasantly smelling substances,
particularly in combination with (other) fragrance substances as described further above.

Thereby preferred is the use of a mixture according to the invention in a composition, preferably a perfume oil, that contains one or several (further) pleasantly and/or unpleasantly smelling substances, whose unpleasant olfactory impression is masked or reduced by the mixture according to the invention and/or whose pleasant olfactory impression is enhanced by the mixture according to the invention, wherein this/these pleasantly and/or unpleasantly smelling substance or one, several or all of these pleasantly and/or unpleasantly smelling substances is or are selected from the group consisting of alcohols, aldehydes, ketones, ethers, esters and carboxylates, preferably ketones and esters, and/or has or have a molar mass in the range of 150 to 285 g/mol.

Herein described in this context is also a method
(a) for masking or reducing the or one or several unpleasant olfactory impressions of one or several unpleasantly smelling substances,
and/or
(b) for enhancing the or one or several pleasant olfactory impressions of one or several pleasantly smelling substances,
comprising the following step:
Mixing of the (a) pleasantly and/or (b) unpleasantly smelling substances with a mixture or fragrance substance mixture according to the invention or, preferably, a first compound (E) and a second compound (Z) as defined herein according to the invention, in a weight ratio as defined herein according to the invention, wherein the amount of mixture or of compounds (E) and (Z) according to the invention is sufficient (a) to enhance the pleasant olfactory impression(s) of the pleasantly smelling substance(s) and/or (b) to mask or to reduce the unpleasant olfactory impression(s) of the unpleasantly smelling substance(s).

As mentioned initially, in the context of the present invention a method for producing a mixture containing or consisting of a first compound (E) and a second compound (Z) is provided, wherein compounds (E) and (Z) are compounds of formula (I) with identical constitutional formula

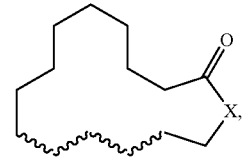

(I)

wherein it applies that one of the four wavy lines denotes a double bond and the remaining wavy lines denote a single bond, respectively, and X is selected from —CH$_2$— and —CH$_2$—CH$_2$—,
and the first compound (E) is trans-configurated and the second compound (Z) is cis-configurated, wherein the weight ratio of compound (E) to compound (Z) in the mixture is in the range of 75:25, preferably of 80:20, to 90:10.

Such a method comprises at least the following steps:
(i) Providing a base mixture containing or consisting of a first compound (E) and a second compound (Z), wherein compounds (E) and (Z) are compounds of formula (I) with identical constitutional formula

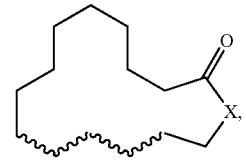

(I)

wherein it applies that one of the four wavy lines denotes a double bond and the remaining wavy lines denote a single bond, respectively, and X is selected from —$CH_2$— and —$CH_2$—$CH_2$—, and the first compound (E) is trans-configurated and the second compound (Z) is cis-configurated, wherein the weight ratio of compound (E) to compound (Z) in the base mixture is lower than 90:10, preferably lower than 80:20, preferably lower than 75:25 or preferably is in the range of lower than 80:20 to 60:30, particularly preferably in the range of 75:25 to 60:30, (ii) performing an acid-catalyzed isomerization, preferably with the use of nitric acid, on compound (Z) contained in the base mixture, so that a mixture is obtained, wherein the weight ratio of compound (E) to compound (Z) is in the range of 75:25, preferably of 80:20, to 90:10.

Preferred embodiments of this method or compounds to be preferably used arise from the preceding description.

Further enrichments of E-isomer are for example possible by means of fractional distillation.

An exemplary conduct of method of a method according to the invention is described in Example 3.

Particularly preferably the mixture according to the invention described herein is a mixture that is produced or producible by using a method according to the invention.

In the following, the present invention will be illustrated in more detail by means of selected examples. Unless otherwise stated, all specifications thereby relate to the weight.

EXAMPLES

Example 1: Perfume Oil P1 Ketones

| Component | wt. proportion |
| --- | --- |
| HEXENYL BENZOATE CIS-3 | 5 |
| PHENYL ACETALDEHYDE DIMETHYL ACETAL | 3 |
| LINALYL ACETATE | 70 |
| APRIFLOREN | 20 |
| LILIAL | 30 |
| FLOROSA | 20 |
| MAJANTOL | 20 |
| MUGETANOL | 5 |
| LINALOOL | 35 |
| ROSE OXIDE | 5 |
| PHENYLETHYL ALCOHOL | 50 |
| ROSAPHEN | 50 |
| GERANYL ACETATE | 20 |
| BENZYL ACETATE | 50 |
| HEDIONE | 120 |
| YLANG OIL TYPE BASE | 5 |
| ISOBUTYL SALICYLATE | 18 |
| DIHYDRO IONONE BETA | 20 |
| IONONE ALPHA | 35 |
| IONONE BETA | 25 |
| ISORALDEINE 70 | 100 |
| ANISALDEHYDE | 20 |
| HELIOTROPIN | 30 |
| METHYL CINNAMATE | 15 |
| COUMARIN | 20 |
| CEDRYL ACETATE | 20 |
| ISO E SUPER | 120 |
| TIMBEROL | 5 |
| PATOULIOEL | 5 |
| BRAHMANOL | 10 |
| | 950 |

A wooden accentuated composition with soft-floral elements of violets and lilies results, rounded off with aromatic components of tonka beans and cinnamon bark.

An addition of 10% (with respect to the total weight of the fragrance substances of the group of ketones contained in the judged fragrance substance mixture) of an isomer mixture of cyclohexadec-8-en-1-one (here: 80% trans-cyclohexadec-8-en-1-one: 20% cis-cyclohexadec-8-en-1-one) makes the composition more harmonious, reduces the spice notes and makes it appear of higher value, cosmetic and elegant.

Example 2: Perfume Oil P2 Esters

| Component | wt. proportion |
| --- | --- |
| ALDEHYDE C 12 LAURIN | 4 |
| VERTOCITRAL | 5 |
| STYROLYL ACETATE | 12 |
| MINTONATE | 10 |
| DIHYDROMYRCENOL | 45 |
| LINALYL ACETATE | 75 |
| AGRUNITRILE | 10 |
| ORANGE OIL | 50 |
| METHYL ANTHRANILATE | 5 |
| ISOBORNYL ACETATE | 10 |
| HEXYL ACETATE | 10 |
| ALDEHYDE C 14 SO CALLED | 45 |
| ALDEHYDE C 18 SO CALLED | 10 |
| MANZANATE | 10 |
| ALLYL CAPRONATE | 5 |
| ALLYL CYCLOHEXYL PROPIONATE | 5 |
| ALLYL HEPTYLATE | 5 |
| DEWFRUIT TYPE BASE | 10 |
| LILIAL | 30 |
| PHENYLETHYL ACETATE | 20 |
| PHENYLETHYL ALCOHOL | 50 |
| CITRONELLYL ACEATE | 20 |
| DAMASCONE DELTA | 10 |
| BENZYL ACETATE | 30 |
| HEDIONE | 75 |
| HEXYL CINNAMIC ALDEHYDE ALPHA | 75 |
| BENZYL SALICYLATE | 30 |
| HEXYL SALICYLATE | 60 |
| MYSORE ACETATE | 30 |
| ISORALDEINE 70 | 30 |
| AGRUMEX HC | 25 |
| HERBAFLORAT | 75 |
| HERBYL PROPIONATE | 35 |
| AMBROCENIDE 10% IN DPG | 4 |
| YSAMBER K | 25 |
| | 950 |

The scent is refreshing-citric, green-fruity, pear-like, smells aromatic of wild berries and has a subtle rounding of tropical wood.

The addition of up to 10%, preferably less than 10% (with respect to the total weight of the fragrance substances of the group of esters contained in the judged fragrance substance mixture) of an isomer mixture of cyclohexadec-8-en-1-one (here: 90% trans-cyclohexadec-8-en-1-one: 10% cis-cyclohexadec-8-en-1-one) gives rise to a mild, aromatic and very near-natural fruitiness. Slightly overaccentuated chemical undertones are reduced. The relative strength of the aroma sensation is enhanced in a pleasant way.

Example 3: Production of a Mixture According to the Invention (Enrichment of E-Isomer by Means of Isomerization (e.g. By Using Globanone or Exaltenone))

45 g Globanone (cyclohexadec-8-en-1-one) (here: 67% (E) and 31% (Z)) are dissolved in 225 ml isopropanol and 3.0 g nitric acid (65%) are added. Subsequently, it is stirred for 8 h at room temperature.

Workup: Soda is added to the batch, it is concentrated on a rotary evaporator and distilled by means of Kugelrohr distillation. It can be proceeded in a corresponding manner starting from an isomer mixture of cyclopentadec-4-en-1-one (exaltenone)—instead of an isomer mixture of cyclohexadec-8-en-1-one—(see the table listed below for details).

Isomerization Results:

| Structure | MW | GC-% educt | GC-% isomerization |
|---|---|---|---|
| Globanone | | | |
| 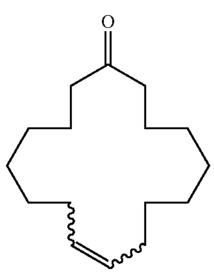 [SMILES: O=C1CCCCCCC=CCCCCCCC1] | 236 | 67% E<br>31% Z | 77% E<br>21% Z |
| Exaltenone | | | |
| 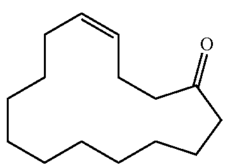 [SMILES: O=C1CC/C=C\CCCCCCCCCC1] | 222 | 3% E<br>95% Z | 82% E<br>16% Z |

Further enrichments of E-isomer are possible, for example, by means of fractional distillation (e.g.: 80% E:20% Z and 90% E:10% Z).

The invention claimed is:

1. A fragrance substance mixture comprising:
   (a) a first compound (E) and a second compound (Z), both having the same chemical formula, wherein the first compound (E) and the second compound (Z) are individually selected from the group consisting of cyclohexadec-8-en-1-one and cyclopentadec-4-en-1-one, and wherein the first compound (E) is trans-configurated and the second compound (Z) is cis-configurated, and
      wherein the weight ratio of the first compound (E) to the second compound (Z) is from 4:1 to 9:1; and
   (b) one or several additional fragrance substances;
      wherein the fragrance substance mixture does not comprise compounds of formula (I) except for the first compound (E) and the second compound (Z) of (a),

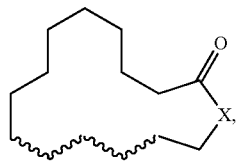

(I)

wherein one of the four wavy lines denotes a double bond and the remaining wavy lines denote a single bond, respectively, and X is selected from —CH$_2$— and —CH$_2$—CH$_2$—.

2. A fragrance substance mixture according to claim 1, wherein the one or several additional fragrance substances is or are selected from the groups consisting of alcohols, aldehydes, ketones, ethers, esters, and carboxylates.

3. A fragrance substance mixture according to claim 1, wherein the one or several additional fragrance substances has or have a molar mass in the range of 150 to 285 g/mol.

4. A fragrance substance mixture according to claim 1, wherein the weight ratio of the total mass of fragrance substances that do not correspond to the first compound (E) and the second compound (Z) to the total mass of the first compound (E) and the second compound (Z) is higher than or equal to 4:1.

5. A fragrance substance mixture according to claim 1 producible by a method comprising the following steps:
   (i) providing a base mixture comprising the first compound (E) and the second compound (Z),
      wherein the weight ratio of the first compound (E) to the second compound (Z) in the base mixture is lower than 9:1,
   (ii) performing an acid-catalyzed isomerization on the second compound (Z) contained in the base mixture, so that a mixture is obtained, wherein the weight ratio of the first compound (E) to the second compound (Z) is in the range of 4:1 to 9:1; and
   (iii) incorporating into the mixture one or several additional fragrance substances.

6. A fragrance substance mixture according to claim 1, wherein the amount of the first compound (E) and the second compound (Z) is sufficient
   (a) to mask or reduce one or several unpleasant olfactory impression(s) of another fragrance substance in the fragrance substance mixture, and/or
   (b) to enhance one or several pleasant olfactory impression(s) of another fragrance substance in the fragrance substance mixture.

7. A fragrance substance mixture according to claim 1, wherein the total amount of the first compound (E) and the second compound (Z) with regard to the total weight of the fragrance substance mixture is 1 wt. % or less.

8. A fragrance substance mixture of claim 1, wherein the fragrance substance mixture comprises cyclohexadec-8-en-1-one and cyclopentadec-4-en-1-one.

9. A fragrance substance mixture according to claim 1, wherein the one or several additional fragrance substances has or have a molar mass in the range of 210 g/mol or less.

10. A fragrance substance mixture according to claim 1, wherein the ratio of the total mass of fragrance substances that do not correspond to the first compound (E) and second compound (Z) to the total mass of compound(s) of the first compound (E) and second compound (Z) is higher than or equal to 9:1.

11. A fragrance substance mixture according to claim 1, wherein the ratio of the total mass of fragrance substances that do not correspond to the first compound (E) and the second compound (Z) to the total mass of compound(s) of the first compound (E) and the second compound (Z) is higher than or equal to 19:1.

12. A fragrance substance mixture according to claim 1, wherein (a) is cyclohexadec-8-en-1-one.

13. A fragrance substance mixture according to claim 1, wherein (a) is cyclopentadec-4-en-1-one.

14. A fragrance substance mixture according to claim 1, wherein the one or several additional fragrance substances is or are selected from the groups consisting of ketones and esters.

* * * * *